(12) United States Patent
Lucio

(10) Patent No.: US 10,905,785 B2
(45) Date of Patent: Feb. 2, 2021

(54) SYSTEM AND METHOD FOR DISINFECTING A CONDUIT

(71) Applicant: 3B Medical, Inc., Winter Haven, FL (US)

(72) Inventor: Albert A. Lucio, Haines City, FL (US)

(73) Assignee: 3B MEDICAL, INC., Winter Haven, FL (US)

( * ) Notice: Subject to any disclaimer, the term of this patent is extended or adjusted under 35 U.S.C. 154(b) by 190 days.

(21) Appl. No.: 16/378,644

(22) Filed: Apr. 9, 2019

(65) Prior Publication Data

US 2019/0314532 A1  Oct. 17, 2019

Related U.S. Application Data

(60) Provisional application No. 62/657,005, filed on Apr. 13, 2018, provisional application No. 62/715,823, filed on Aug. 8, 2018.

(51) Int. Cl.

| | |
|---|---|
| *A61L 2/10* | (2006.01) |
| *A61L 2/00* | (2006.01) |
| *A61M 16/00* | (2006.01) |
| A61M 16/06 | (2006.01) |
| A61L 2/24 | (2006.01) |

(52) U.S. Cl.
CPC .............. *A61L 2/0047* (2013.01); *A61L 2/10* (2013.01); *A61M 16/0066* (2013.01); A61L 2/24 (2013.01); A61L 2202/24 (2013.01); A61M 16/06 (2013.01); A61M 2209/10 (2013.01)

(58) Field of Classification Search
CPC ...... A61L 2/0047; A61L 2/10; A61L 2202/11; A61L 2202/14; A61L 2202/24; A61M 16/0066; A61M 2209/10
See application file for complete search history.

(56) References Cited

U.S. PATENT DOCUMENTS

2018/0104368 A1* 4/2018 Dobrinsky ................ A61L 2/10

OTHER PUBLICATIONS

Howard III, George B., "Executive Summary, CleanPAP," Triple Cs, LLC, Mr. Pior "Peter" Czapla, inventor. 2019.

* cited by examiner

*Primary Examiner* — Timothy C Cleveland
(74) *Attorney, Agent, or Firm* — Carlson, Gaskey & Olds, P.C.

(57) ABSTRACT

This disclosure relates to a system and method for disinfecting a conduit, such as a conduit for use in a continuous positive airway pressure (CPAP) system. An example system according to this disclosure includes a sheath a probe magnetically suspended within the sheath. The probe includes an ultraviolet light source configured to emit ultraviolet light. Further, the probe is spaced-apart from an inner dimension of the sheath to allow a conduit to pass between the probe and the sheath.

20 Claims, 6 Drawing Sheets

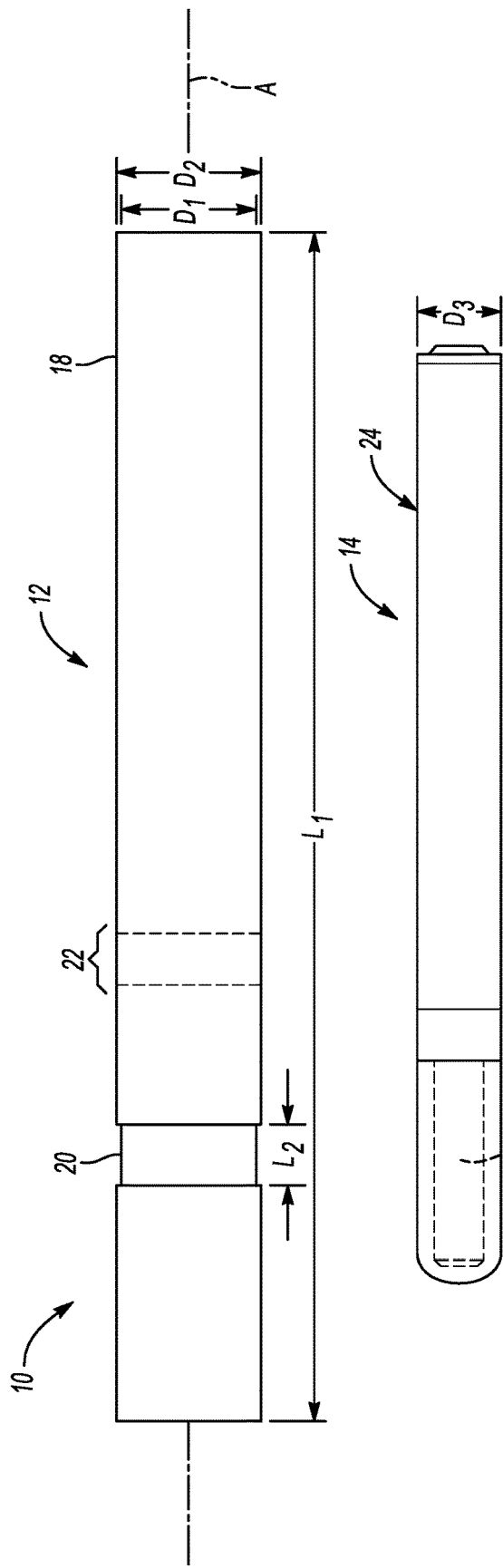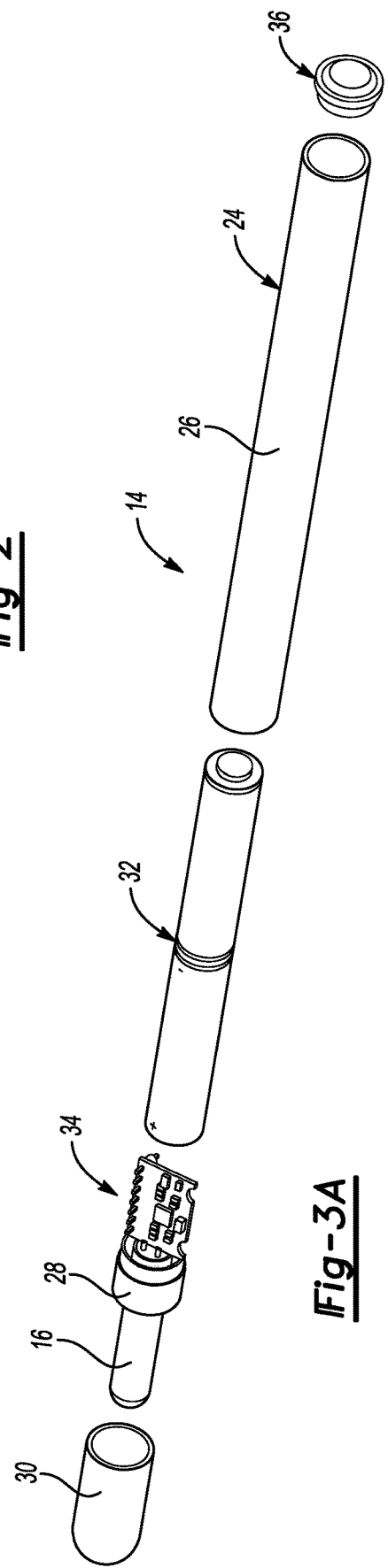
Fig-2
Fig-3A

SYSTEM AND METHOD FOR DISINFECTING A CONDUIT

RELATED APPLICATIONS

This application claims the benefit of U.S. Provisional Application No. 62/657,005, filed Apr. 13, 2018. This application also claims the benefit of U.S. Provisional Application No. 62/715,823, filed Aug. 8, 2018. The '005 and '823 Provisional Applications are herein incorporated by reference in their entirety.

TECHNICAL FIELD

This disclosure relates to a system and method for disinfecting a conduit, such as a conduit for use in a continuous positive airway pressure (CPAP) system.

BACKGROUND

CPAP represents a treatment for patients with breathing problems. Such problems typically manifest themselves at night while the patient is asleep. One such problem is sleep apnea.

The CPAP treatment uses mild air pressure to keep airways open, particularly when a patient is sleeping. CPAP systems have several components. The first is a flow generator, which is essentially a pump that creates a stream of air. Many flow generators include a humidifier, which is typically attached to the flow generator or integrally formed with the same. Humidifiers are configured to heat and moisten the air flow from the flow generator, which reduces the likelihood that a patient will experience discomfort from breathing dry air for a prolonged period. CPAP systems also include a conduit (i.e., a tube or hose) fluidly coupling a mask apparatus to the flow generator. The mask is affixed to the mouth and/or nose of a patient. Additionally, CPAP systems include various couplings, fittings, seals, valves, etc., that establish the fluid connection between the flow generator and the patient.

During use over the course of days, weeks, and months, it is recommended that the components of a CPAP system be cleaned and disinfected to prevent buildup of bacteria, for example. Disinfection is recommended to reduce health risks. CPAP systems and their associated components are typically cleaned manually by a patient using soap and water.

SUMMARY

A system according to an exemplary aspect of this disclosure includes, among other things, a sheath and a probe magnetically suspended within the sheath. The probe includes an ultraviolet light source configured to emit ultraviolet light. Further, the probe is spaced-apart from an inner dimension of the sheath to allow a conduit to pass between the probe and the sheath.

In a further non-limiting embodiment of the foregoing system, at least one of the sheath and the probe includes a magnet configured to magnetically suspend the probe within the sheath.

In a further non-limiting embodiment of any of the foregoing systems, the sheath includes a magnetic ring, and the probe includes one of a magnetic ring and a ring made of a ferromagnetic material attracted to the magnetic ring of the sheath.

In a further non-limiting embodiment of any of the foregoing systems, the magnetic ring of the sheath is a permanent magnet.

In a further non-limiting embodiment of any of the foregoing systems, the probe includes a controller configured to selectively activate the ultraviolet light source.

In a further non-limiting embodiment of any of the foregoing systems, the probe further includes an activation button, and the controller is configured to activate the ultraviolet light source only when the activation button has been depressed and when the probe is within the sheath.

In a further non-limiting embodiment of any of the foregoing systems, the probe includes a power source, and the controller is configured to selectively direct power from the power source to the ultraviolet light source to activate the ultraviolet light source.

In a further non-limiting embodiment of any of the foregoing systems, the sheath is made of an opaque material over a majority of a length of the sheath, and the sheath includes a tinted lens along a portion of the length of the sheath.

In a further non-limiting embodiment of any of the foregoing systems, the ultraviolet light source is configured to emit UV-C light.

In a further non-limiting embodiment of any of the foregoing systems, an inner diameter of the sheath is variable along a length of the sheath.

In a further non-limiting embodiment of any of the foregoing systems, the inner diameter of the sheath includes a plurality of spaced-apart ridges projecting radially inward from the remainder of the inner diameter of the sheath.

In a further non-limiting embodiment of any of the foregoing systems, the sheath and the probe are substantially cylindrical.

In a further non-limiting embodiment of any of the foregoing systems, the conduit is configured for use with a continuous positive airway pressure (CPAP) system.

A method according to an exemplary aspect of the present disclosure includes, among other things, disinfecting a conduit by passing the conduit within a sheath and over a probe emitting ultraviolet light. Further, the probe is suspended magnetically within the sheath.

In a further non-limiting embodiment of the foregoing method, the sheath includes a magnetic ring and the probe includes one of a magnetic ring and a ring made of a ferromagnetic material attracted to the magnetic ring of the sheath.

In a further non-limiting embodiment of any of the foregoing methods, the probe emits ultraviolet light only when the probe is within the sheath.

In a further non-limiting embodiment of any of the foregoing methods, the probe further includes an activation button, and the probe only emits ultraviolet light when the activation button has been depressed and when the probe is within the sheath.

In a further non-limiting embodiment of any of the foregoing methods, the sheath is made of an opaque material over a majority of a length of the sheath, and the sheath includes a tinted lens along a portion of the length of the sheath.

In a further non-limiting embodiment of any of the foregoing methods, the probe emits UV-C light.

In a further non-limiting embodiment of any of the foregoing methods, an inner diameter of the sheath is variable along a length of the sheath.

BRIEF DESCRIPTION OF THE DRAWINGS

FIG. 2 is a top view of the sheath and probe of FIG. 1.

FIG. 3A is a perspective, exploded view of the probe of FIG. 1.

DETAILED DESCRIPTION

This disclosure relates to a system and method for disinfecting a conduit, such as a conduit for use in a CPAP system. In particular, an example system according to this disclosure includes a sheath and a probe magnetically suspended within the sheath. The probe includes an ultraviolet light source configured to emit ultraviolet light. Further, the probe is spaced-apart from an inner dimension of the sheath to allow a conduit to pass between the probe and the sheath. The system (and its use) provides a number of benefits, which will be appreciated from the below description. Among other benefits, this disclosure provides a convenient and easy-to-use technique for disinfecting conduits of CPAP systems, for example. This disclosure also provides for increased safety, by virtue of the sheath shielding a user from ultraviolet light emitted during the disinfection process.

Figure 1:
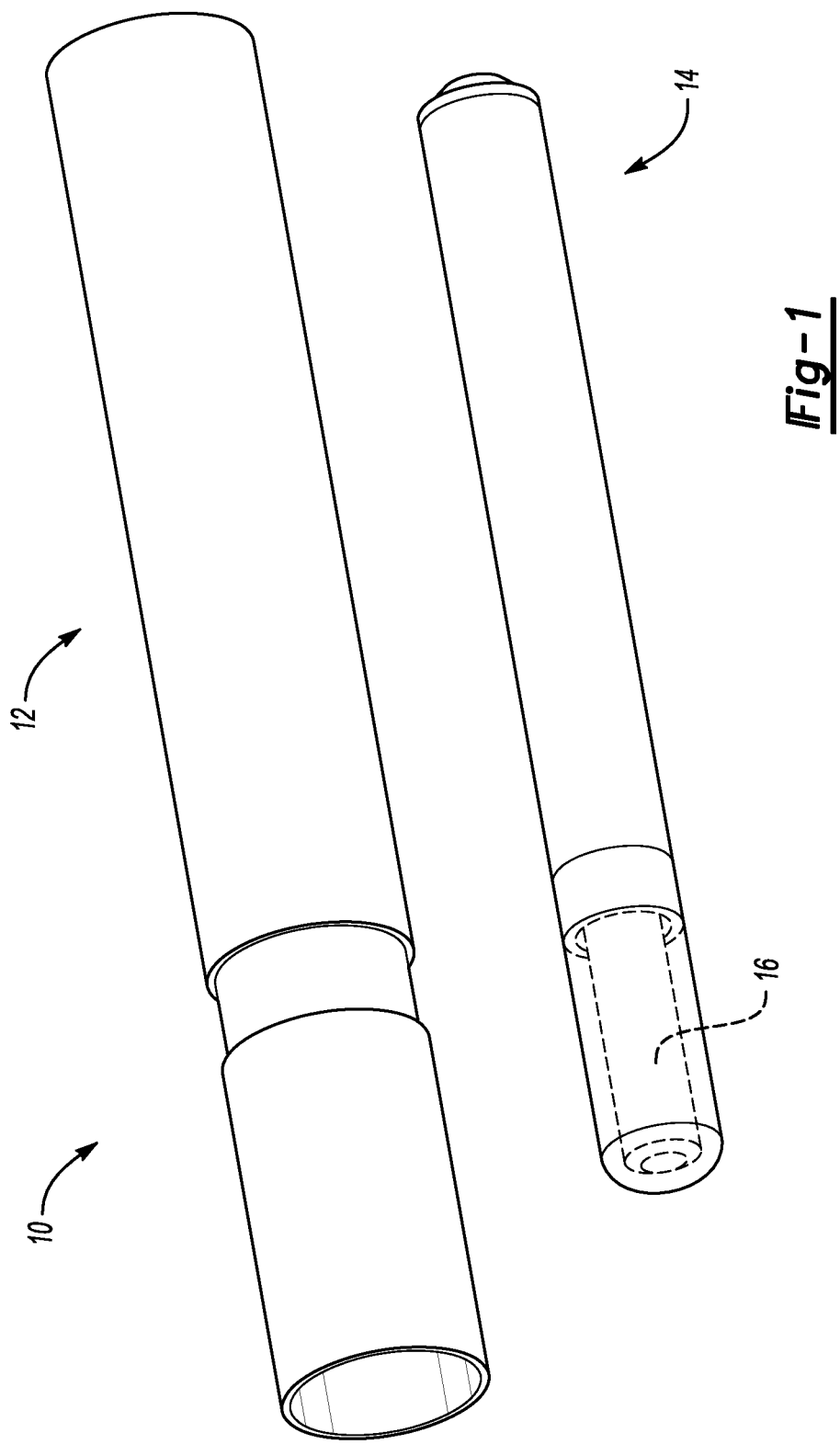
FIG. 1 illustrates an example system according to this disclosure, and in particular is a perspective view of an example sheath and probe arranged side by side.

With reference to the drawings, FIGS. 1 and 2 illustrate an example system 10 configure to disinfect a conduit, such as a conduit of a CPAP system. The conduit may be the tube or hose which connects a flow generator to a mask, for example. This disclosure is not limited to use disinfecting conduits for CPAP systems, however, and extends to other types of conduits that may require disinfection.

The system 10, in this example, includes a sheath 12 and a probe 14. The probe 14, in this example, includes an ultraviolet (UV) light source 16 configured to emit UV light. The UV light source 16 may include one or more light emitting diodes. In one particular example, the UV light source 16 is configured to emit UV-C light, which is a subtype of UV light especially suited for disinfection. Specifically, UV-C is relatively short-wavelength UV light, which is known to kill or inactivate microorganisms such as bacteria.

The sheath 12 and probe 14 are shown side by side in FIGS. 1 and 2. In use, however, the probe 14 is magnetically suspended within the sheath 12. An example magnetic arrangement configured to magnetically suspend the probe 14 relative to the sheath 12 will be discussed in detail below. By magnetically suspending (sometimes called magnetic levitation) the probe 14, the probe 14 is spaced-apart from an inner dimension of the sheath 12, which allows a user to pass a conduit through the sheath 12 and over the probe 14. As the conduit is passed over the probe 14, the conduit is exposed to UV light from the UV light source 16, which disinfects the conduit.

With reference to FIG. 2, the sheath 12, in this example, is provided by a substantially cylindrical housing 18 about an axis A. The housing 18 has an inner dimension $D_1$ and an outer dimension $D_2$. The difference between the inner and outer dimensions $D_1$, $D_2$ is the thickness of the housing 18, which is substantially uniform along the housing 18 in this example. The housing 18 has an overall length $L_1$, the majority of which is provided by an opaque material, such as plastic. The opaque material completely prevents light from being emitted therethrough.

The housing 18, in this example, also includes a tinted lens 20 over a portion $L_2$ of the length $L_1$. The portion $L_2$ is a small portion of the length $L_1$, and in one example is about 5-10% of the length $L_1$. Further, the portion $L_2$ is spaced-apart from the ends of the housing. The tinted lens 20 is configured to filter UV light, and in particular UV-C light, such that a user can look through the tinted lens 20 without damaging their eyesight.

The sheath 12 further includes a magnetic ring 22, in this example. The magnetic ring 22 is shown in phantom in FIG. 2. The magnetic ring 22 is integrated into the housing 18, and has a thickness substantially the same as the housing 18. In this example, the magnetic ring 22 is a continuous ring, or hoop, extending about the axis A. The magnetic ring 22 is made of a magnetic material and is configured to generate a magnetic field. The magnetic ring 22 is a permanent magnet in one example. Other types of magnetic rings come within the scope of this disclosure.

Figure 3B:
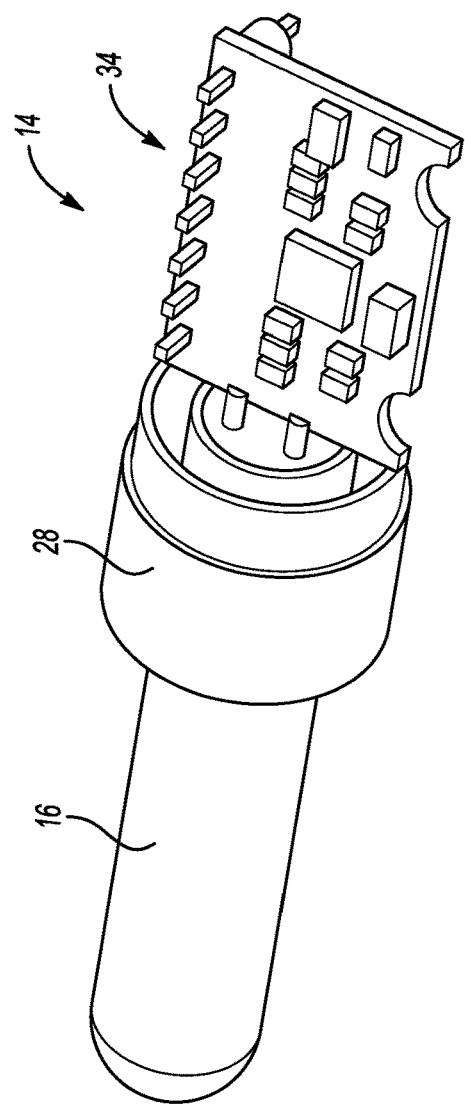
FIG. 3B is a perspective view of a portion of the probe.

Turning to the probe 14, the probe 14 is provided by a substantially cylindrical body 24 having an outer dimension $D_3$. The outer dimension $D_3$ is less than the inner dimension $D_1$ of the sheath 12. With reference to FIGS. 3A and 3B, the body 24 includes three components, a casing 26, a metallic ring 28, and a light cover 30.

The casing 26 is a substantially cylindrical body configured to house a power source 32, which in this example includes one or more batteries, and a printed circuit board 34. The light cover 30 is a transparent cover configured to protect the UV light source 16, and the metallic ring 28 is provided between the battery casing 26 and the light cover 30. While shown in a particular location, the metallic ring 28 could be provided at other locations along the length of the probe 14.

The metallic ring 28, in this example, is made either of a ferromagnetic material, such as iron, nickel, cobalt, or their alloys, or is provided by a magnet. In either instance, the metallic ring 28 is configured to react to the magnetic field generated by the magnetic ring 22 such that the probe 14 is suspended and held in a substantially stable position within the sheath 12.

In one example, the magnetic ring 22 is configured to attract the metallic ring 28, and the force of attraction, coming from all radial directions, is sufficient to magnetically suspend the probe 14 within the sheath 12 and to hold the probe 14 in a stable position within the sheath 12. In another example, the sheath 12 includes two magnetic rings spaced-apart from one another along the axis A, and those rings generate magnetic fields that repel the metallic ring 28. Thus, the probe 14 is magnetically suspended and held in a stable position between the two spaced-apart magnetic rings. Other magnetic arrangements come within the scope of this disclosure.

The printed circuit board 34 includes a controller, which may include one or more electronic components such as microprocessors. The power source 32 is electrically coupled to the UV light source 16 via the printed circuit board 34, and the controller is configured to selectively activate the UV light source 16 when certain conditions are met. In one example, the controller is configured to activate the UV light source 16 only when an activation button 36, such as an on-off button, mounted to an end of the probe 14 is depressed (i.e., in the "ON" position) and when the probe 14 is within the sheath 12. The controller may determine that the probe 14 is within the sheath by virtue of the proximity of the probe 14 to a magnetic field generated by the magnetic ring 22. To this end, the printed circuit board 34 may include or be in communication with one or more sensors configured to detect a magnetic field, and the controller may be configured to interpret signals from such sensors to determine a proximity to the magnetic ring 22. In this way, the UV light source 16 is activated only when the user desires it (i.e., by virtue of the activation button 36 being depressed) and when it is safe to do so (i.e., when the UV light will be shielded by the sheath 12).

As another precaution, the controller may be configured to automatically turn off the UV light source after a predefined time period. For instance, after the activation button 36 has been depressed, the controller may interrupt the flow of power from the power source 32 to the UV light source 16 after a predefined time period. The time period may be 20 seconds in one example. In other examples, the time period may be between 10 and 60 seconds. This disclosure extends to other time periods.

It should be understood that the controller may be programmed with executable instructions for interfacing with and operating the various components of the system 10, and in particular the probe 14, including but not limited to those shown in the figures and discussed herein. It should also be understood that the controller may additionally include a combination of hardware and software, and specifically may include a processing unit and non-transitory memory for executing the various control strategies and modes of the probe 14.

Figure 4:
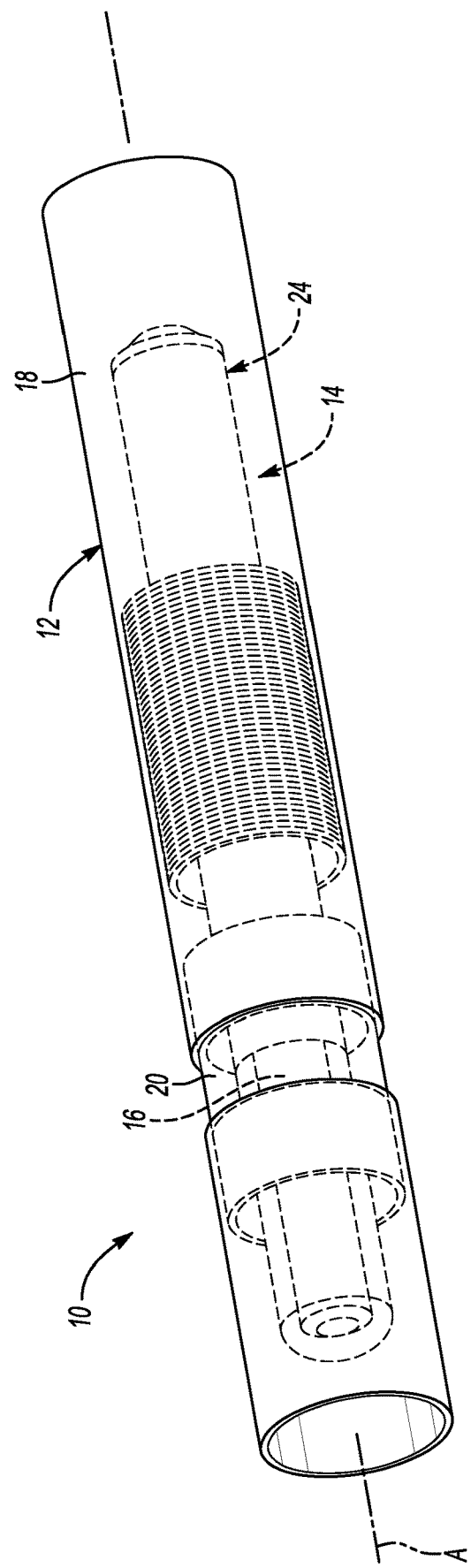
FIG. 4 is a perspective view of the system with the sheath drawn semi-transparently, in order to show an example arrangement of the probe within the sheath.

FIG. 4 illustrates the probe 14 within the sheath 12. In FIG. 4, probe 14 is magnetically suspended within the sheath 12 such that the body 24 of the probe 14 is spaced-apart from the inner dimension of the sheath 12. In this example, the UV light source 16 is axially aligned, relative to the axis A, with the tinted lens 20. Using the tinted lens 20, a user can determine whether the probe 14 is properly positioned in the sheath 12.

In the position of FIG. 4, the magnetic arrangement between the sheath 12 and the probe 14 magnetically suspends the probe 14 within the sheath 12 and holds the probe 14 stably within the sheath 12. The magnetic forces at play are also sufficient to hold the probe 14 axially in place as a conduit passes through the sheath 12 and over the probe 14.

Figure 5:
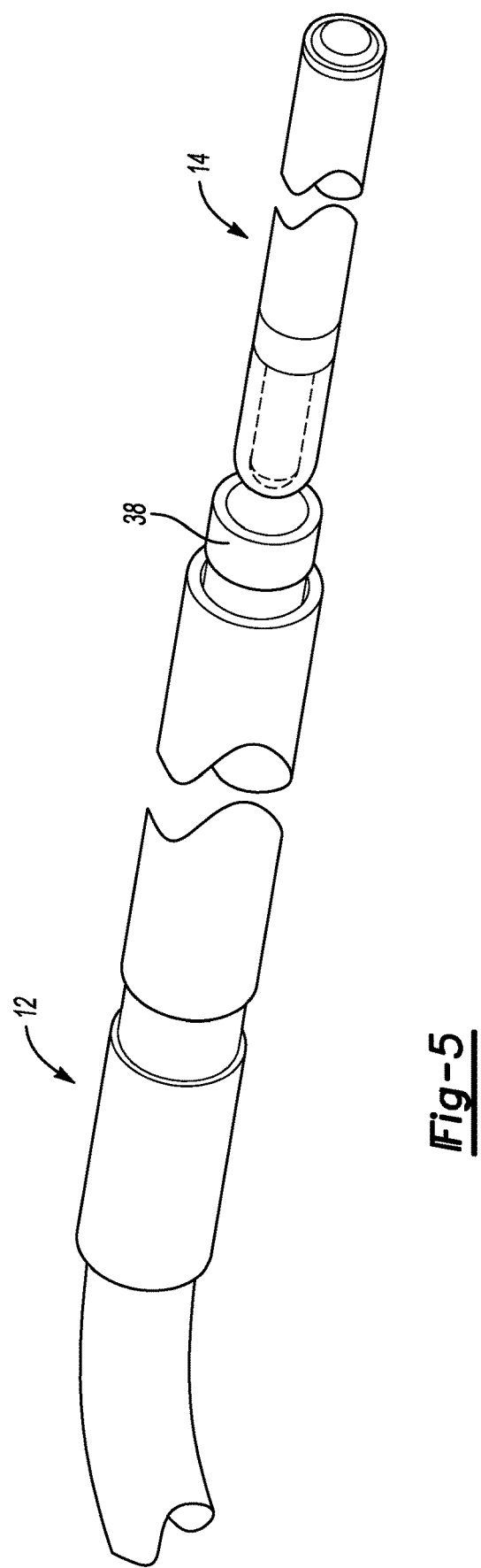
FIG. 5 is a perspective view of the system with a conduit passing through the sheath.

FIG. 5 illustrates a conduit 38 relative to the sheath 12 and the probe 14. In FIG. 5, the probe 14 is removed from the sheath 12 for ease of reference, but in practice the conduit 38 would be passed over the probe 14 while the probe 14 is magnetically suspended within the sheath 12, as shown relative to FIG. 4. With the probe 14 magnetically suspended and stabilized, a user can essentially feed the conduit 38 through the sheath 12 and over the probe 14. As the conduit 38 is fed through the sheath 12 and over the probe 14, the UV light emitted from the UV light source 16 disinfects the conduit 38, and specifically disinfects the interior of the conduit 38. It should be noted that the magnetic forces at play between the sheath 12 and the probe 14 are sufficient to prevent movement of the conduit 38 from causing the probe 14 to slide out of the sheath 12.

As mentioned above, the conduit 38 may be a conduit, such as a hose, for use in a CPAP system. The dimensions of the sheath 12 and probe 14 may correspond to those of known CPAP hoses. For instance, known CPAP hoses have inner dimensions (i.e., inner diameters) ranging from about 13 mm to 22 mm. As such, the inner dimension $D_1$ of the sheath 12 may be greater than 22 mm and the outer dimension $D_3$ of the probe 14 may be less than 13 mm, in one example. This disclosure extends to other dimensions, however, especially when used outside the CPAP context.

Figure 6B:
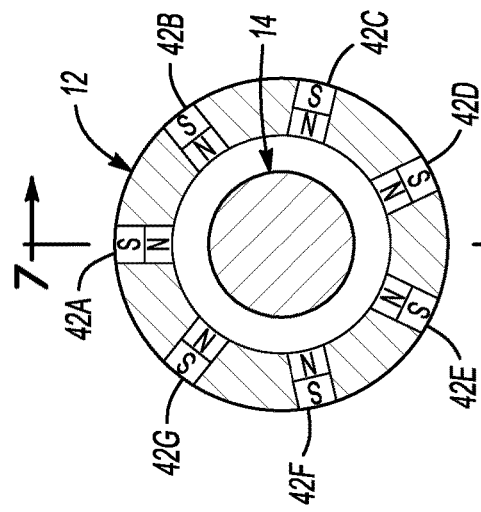
FIG. 6B is a schematic end view of the example sheath and probe, and schematically illustrates an example magnet arrangement.
Figure 6A:
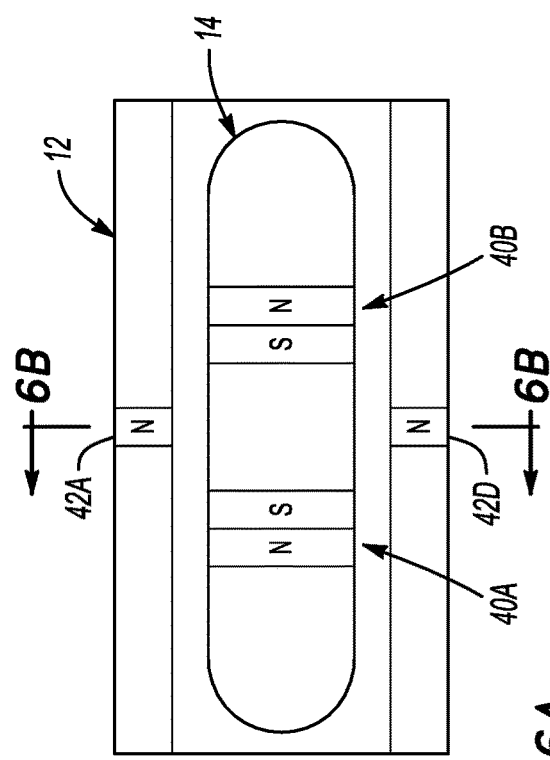
FIG. 6A is a schematic side view of an example sheath and probe, and schematically illustrates an example magnet arrangement.

FIGS. 6A and 6B schematically illustrate an example magnet arrangement configured to suspend the probe 14 relative to the sheath 12. While a magnetic ring 22 and a metallic ring 28 are discussed above, this disclosure extends to other arrangements (such as that of FIGS. 6A and 6B). In FIG. 6A, the probe 14 includes a first magnet 40A and a second magnet 40B spaced-apart from the first magnet 40A along the length of the probe 14. The first and second magnets 40A, 40B are arranged such that like poles face one-another. In this example, the south poles of the first and second magnets 40A, 40B face one another. The magnets 40A, 40B may be rare-earth, permanent magnets, and may be substantially cylindrically or disc-shaped, as examples.

The sheath 12 includes one or more magnets configured to attract the probe 14. In this example, the sheath 12 includes a plurality of magnets 42A-42G, as shown in FIG. 6B. The magnets 42A-42G may be rare-earth, permanent magnets. While seven magnets 42A-42G are shown in FIG. 6B, this disclosure extends to sheaths 12 including additional or fewer magnets. The magnets 42A-42G are each arranged such that they are substantially equally spaced-apart from one another about the circumference of the sheath 12. The magnets 42A-42G may be replaced and provided by a single magnetic ring, in one example. In another example, the magnets 42A-42G may be replaced and provided by an electromagnet configured to attract the probe 14.

The magnets 42A-42G are arranged axially between the magnets 40A, 40B. Further, the magnets 42A-42G are arranged such that an opposite pole (e.g., a north pole) to that of the adjacent poles (e.g., south poles) of the first and second magnets 40A, 40B faces radially inward. In this example, the north poles of the magnets 42A-42G face radially inward toward the probe 14, and thus the magnets 42A-42G attract the magnets 40A, 40B radially. Such attraction serves to magnetically suspend the probe 14 within the sheath 12, and resists axial movement of the probe 14 that may be caused by friction between the probe 14 and the conduit 38 as the conduit 38 passes over the probe 14. Further, because the first and second magnets 40A, 40B are spaced-apart from one another, the magnets 42A-42G are capable of keeping the probe 14 substantially in place even if there is some small of axial movement of the probe 14 along the length of the sheath 12. While FIGS. 6A and 6B illustrate one example magnet arrangement, other magnet arrangements come within the scope of this disclosure. For instance, the arrangement may be essentially be reversed. That is, the sheath 12 may include spaced-apart magnets (such as the magnets 40A, 40B) and the probe 14 may include magnets like 42A-42G.

Figure 7:
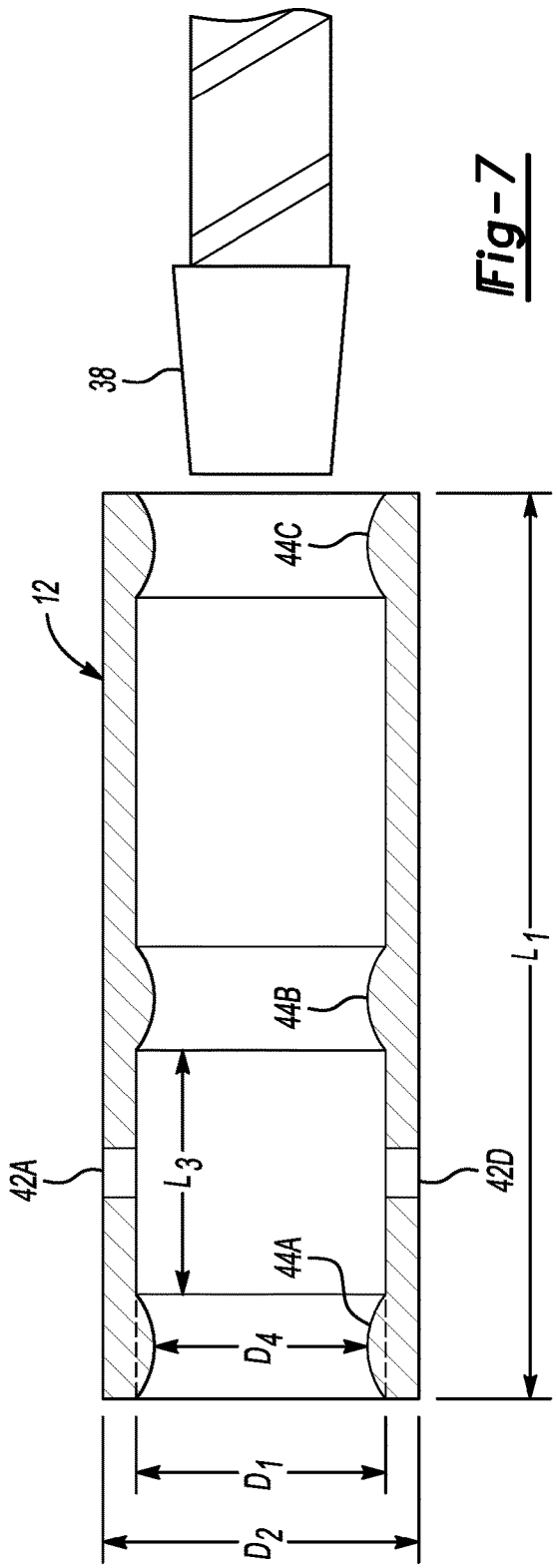
FIG. 7 is a cross-sectional view of the sheath, and in particular illustrates an example inner diameter sheath profile.

In practice, the probe 14 may not always be perfectly suspended within the sheath 12. Rather, the probe 14 may become off-centered, and then come into contact with one side of the sheath 12. In such situations, it may become difficult to maneuver the conduit 38 relative to the probe 14. In the example of FIG. 7, the inner diameter $D_1$ of the sheath 12 is variable along the length $L_1$ of the sheath 12. In particular, the inner diameter $D_1$ of the sheath 12 includes three spaced-apart ridges 44A-44C. The ridges 44A-44C are projections extending radially inward to a dimension $D_4$, which is less than the remainder of the inner diameter $D_1$ of the sheath 12. The ridges 44A-44C each extend circumferentially about the entire inner diameter of the sheath 12 in this example, but that is not required in all examples.

The ridges 44A-44C are spaced-apart from one another such that the probe 14 does not come into contact with the inner diameter $D_1$ along the entire length of the probe 14. As such, in this example, there will always be a gap between the inner diameter $D_1$ and the outer surface of the probe 14 at some point along the length of the probe 14. In this way, it is relatively easy for a user to navigate the conduit 38 between the sheath 12 and the probe 14.

In one example of this disclosure, the two ridges 44A, 44B on opposite axial sides of the magnets 42A-42G are spaced-apart from one another by a distance $L_3$. In one particular example, the ridges 44A, 44B are spaced-apart from the magnets 42A-42G in opposite directions by a distance equal to about half of $L_3$. In this way, the probe 14 is prevented from coming into direct contact with the magnets 42A-42G, which may otherwise have made it relatively difficult to pass the conduit 38 over the probe 14.

Figure 8A:
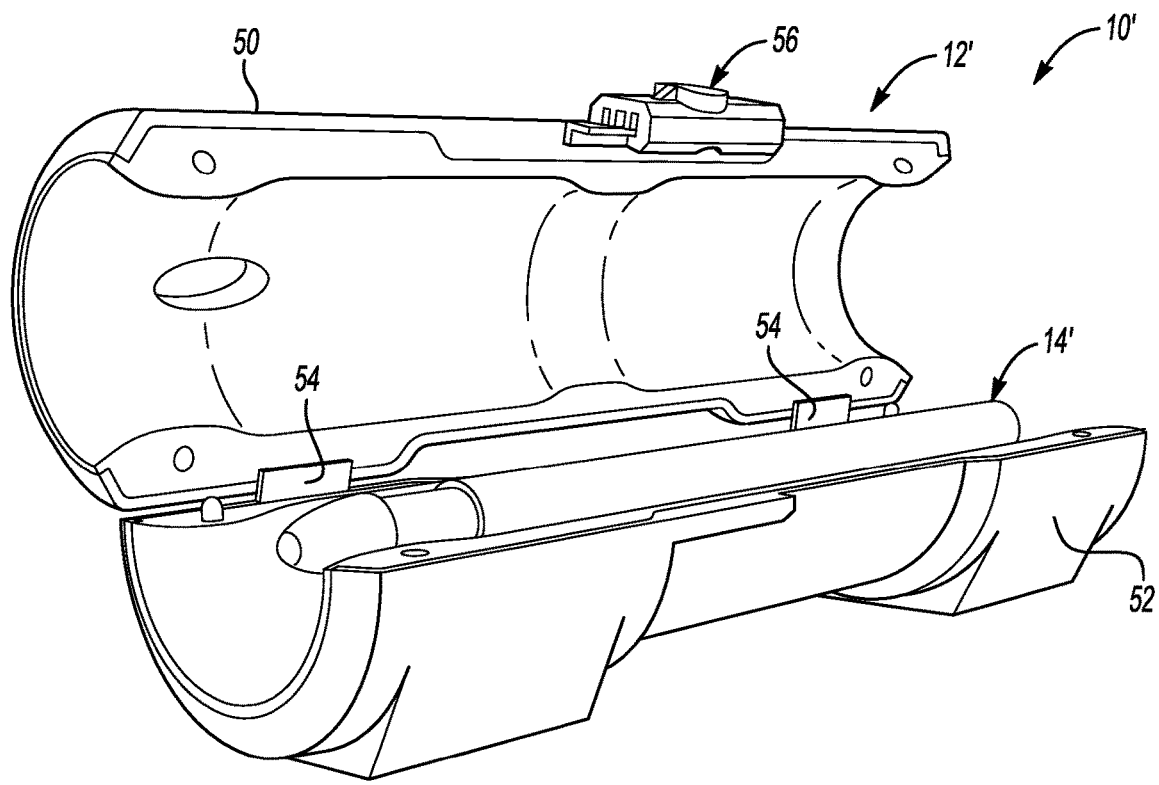
FIG. 8A illustrates another example system with a hinged sheath in an open position.
Figure 8B:
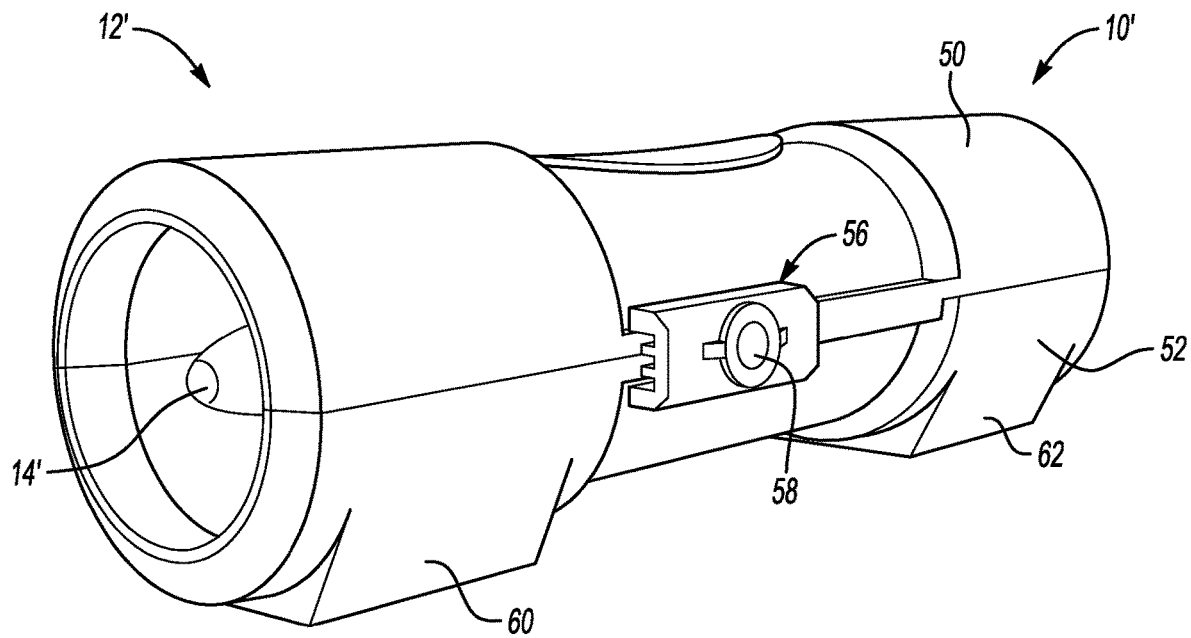
FIG. 8B illustrates the system of FIG. 8A with the sheath in the closed position.

FIGS. 8A and 8B illustrate another example system 10' according to this disclosure. In this embodiment, the system 10' includes a sheath 12' and a probe 14' substantially as described above, with the main exceptions being that the sheath 12' is configured to open and close by movement about a hinge, and is further configured to lock when closed. In particular, in this example, the housing 18' of the sheath 12' is broken into two halves, and the top half 50 is rotatable relative to the bottom half 52 about a hinge 54 between an open position (FIG. 8A) and a closed position (FIG. 8B). When in the open position, it may be easier to arrange the probe 14' and/or conduit within the sheath 12'. When in the closed position, the halves 50, 52 are lockable relative to one another by a sliding lock 56. The sliding lock 56 is configured to slide along the length of the sheath 12' between a first position in which the halves are moveable relative to one another (FIG. 8A), and a second position in which the halves are held in the closed position (FIG. 8B). Further, the sliding lock 56 may include a safety switch 58. In one example, the safety switch 58 is magnetic and is configured to lock the sliding lock 56 in the second position when the system 10' is on (i.e., when the probe 14' is emitting UV light). Finally, for stability, the bottom half 52 of the sheath 12' in this example includes two feet 60, 62 which are relatively flat at the bottom thereof.

It should be understood that terms such as "axial," "radial," and "circumferential" are used above with reference to the normal use of the system 10. Further, these terms have been used herein for purposes of explanation, and should not be considered otherwise limiting. Terms such as "generally," "substantially," and "about" are not intended to be boundaryless terms, and should be interpreted consistent with the way one skilled in the art would interpret those terms.

Although the different examples have the specific components shown in the illustrations, embodiments of this disclosure are not limited to those particular combinations. It is possible to use some of the components or features from one of the examples in combination with features or components from another one of the examples.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A system, comprising:
   a sheath; and
   a probe magnetically suspended within the sheath, the probe including an ultraviolet light source configured to emit ultraviolet light, the probe arranged relative to the sheath such that a conduit may pass between the probe and the sheath.

2. The system as recited in claim 1, wherein at least one of the sheath and the probe includes a magnet configured to magnetically suspend the probe within the sheath.

3. The system as recited in claim 2, wherein:
   the sheath includes a magnetic ring, and
   the probe includes one of a magnetic ring and a ring made of a ferromagnetic material attracted to the magnetic ring of the sheath.

4. The system as recited in claim 3, wherein the magnetic ring of the sheath is a permanent magnet.

5. The system as recited in claim 1, wherein the probe includes a controller configured to selectively activate the ultraviolet light source.

6. The system as recited in claim 5, wherein:
   the probe further includes an activation button, and
   the controller is configured to activate the ultraviolet light source only when the activation button has been depressed and when the probe is within the sheath.

7. The system as recited in claim 5, wherein:
   the probe includes a power source, and
   the controller is configured to selectively direct power from the power source to the ultraviolet light source to activate the ultraviolet light source.

8. The system as recited in claim 1, wherein:
   the sheath is made of an opaque material over a majority of a length of the sheath, and
   the sheath includes a tinted lens along a portion of the length of the sheath.

9. The system as recited in claim 1, wherein the ultraviolet light source is configured to emit UV-C light.

10. The system as recited in claim 1, wherein an inner diameter of the sheath is variable along a length of the sheath.

11. The system as recited in claim 10, wherein the sheath includes a plurality of spaced-apart ridges projecting radially inward.

12. The system as recited in claim 1, wherein the sheath and the probe are substantially cylindrical.

13. The system as recited in claim 1, wherein the conduit is configured for use with a continuous positive airway pressure (CPAP) system.

14. A method, comprising:
   disinfecting a conduit by passing the conduit within a sheath and over a probe emitting ultraviolet light, the probe suspended magnetically within the sheath.

15. The method as recited in claim 14, wherein the sheath includes a magnetic ring and the probe includes one of a magnetic ring and a ring made of a ferromagnetic material attracted to the magnetic ring of the sheath.

16. The method as recited in claim 14, wherein the probe emits ultraviolet light only when the probe is within the sheath.

17. The method as recited in claim 16, wherein the probe further includes an activation button, and wherein the probe only emits ultraviolet light when the activation button has been depressed and when the probe is within the sheath.

18. The method as recited in claim 14, wherein:
the sheath is made of an opaque material over a majority of a length of the sheath, and
the sheath includes a tinted lens along a portion of the length of the sheath.

19. The method as recited in claim 14, wherein the probe emits UV-C light.

20. The method as recited in claim 14, wherein an inner diameter of the sheath is variable along a length of the sheath.

* * * * *